(12) United States Patent
Lind et al.

(10) Patent No.: US 6,190,394 B1
(45) Date of Patent: Feb. 20, 2001

(54) MEDICAL RETRIEVAL BASKET

(75) Inventors: Stuart J. Lind, Edina; Eugene C. Karels, Bloomington, both of MN (US)

(73) Assignee: Annex Medical, Inc., Minnetonka, MN (US)

( * ) Notice: Under 35 U.S.C. 154(b), the term of this patent shall be extended for 0 days.

(21) Appl. No.: 09/435,199

(22) Filed: Nov. 5, 1999

(51) Int. Cl.$^7$ ................................................. A61B 17/22
(52) U.S. Cl. ........................................................ 606/127
(58) Field of Search .............................. 606/127, 128, 606/106

(56) References Cited

U.S. PATENT DOCUMENTS

| | | | |
|---|---|---|---|
| 2,918,919 | * 12/1959 | Wallace | 606/127 |
| 2,943,626 | 7/1960 | Dormia | 128/328 |
| 3,008,467 | * 11/1961 | Morris | 606/127 |
| 4,046,149 | * 9/1977 | Komiya | 606/127 |
| 4,046,150 | * 9/1977 | Schwartz et al. | 606/127 |
| 4,198,960 | 4/1980 | Utsugi | 128/6 |
| 4,299,225 | 11/1981 | Glassman | 128/328 |
| 4,347,846 | 9/1982 | Dormia | 128/328 |
| 4,590,938 | 5/1986 | Segura et al. | 128/328 |
| 4,611,594 | 9/1986 | Grayhack et al. | 128/328 |
| 4,612,931 | 9/1986 | Dormia | 128/328 |
| 4,625,726 | 12/1986 | Duthoy | 128/328 |
| 4,633,871 | 1/1987 | Shinozuka | 128/321 |
| 4,807,626 | 2/1989 | McGirr | 128/328 |
| 5,057,114 | 10/1991 | Wittich et al. | 606/127 |
| 5,064,428 | 11/1991 | Cope et al. | 606/127 |
| 5,176,688 | 1/1993 | Narayan et al. | 606/128 |
| 5,330,482 | 7/1994 | Gibbs et al. | 606/113 |
| 5,496,330 | 3/1996 | Bates et al. | 606/127 |
| 5,792,145 | 8/1998 | Bates et al. | 606/127 |
| 5,944,728 | 8/1999 | Bates | 606/127 |
| 6,093,196 | * 7/2000 | Okada | 606/127 |

* cited by examiner

Primary Examiner—Michael H. Thaler

(57) ABSTRACT

A medical retrieval basket for removing objects such as urinary and biliary calculi from the body. The basket comprises an elongated flexible tube and a cage which is extendible from the distal end of the tube and can be collapsed by withdrawing into the tube by means of an actuation cable which passes through the tube. The cage consists of a plurality of flexible elements which are outwardly disposed to form a space for entrapping objects. The flexible elements are constructed of a shape memory material, allowing the cage to resume its original configuration when extended from the tube. The configuration of the cage is such that by means of rotating the cage, differing sizes, cross sectional shapes and/or spacing of the flexible elements may be presented to a given portion of the object to be removed. Rotation of the cage is controlled more precisely using an actuation cable constructed of nickel titanium.

10 Claims, 2 Drawing Sheets

*Fig. 5a*          *Fig. 5b*
*Fig. 5c*          *Fig. 5d*

MEDICAL RETRIEVAL BASKET

BACKGROUND FIELD OF THE INVENTION

This invention relates to medical retrieval baskets for removing objects from a body, particularly calculi from the urinary and biliary systems.

BACKGROUND DESCRIPTION OF PRIOR ART

Medical instruments are currently in use which reduce the invasiveness and potential trauma previously associated with various medical procedures. One such procedure is the removal of objects, such as kidney stones and gall stones, from the body. Various surgical devices are available which allow objects to be removed from the body without requiring major surgery. One type of surgical device is a mechanical retrieval basket. Typically, such instruments consist of 3 or more flexible elements joined at their distal and proximal ends and formed in the shape of a basket, or cage. This cage is attached to an actuation wire or cable which passes through the lumen of a small diameter flexible tube. By manually manipulating the actuation cable at the proximal end of the tube, the cage can be retracted into the tube. This adjustment is normally accomplished using a sliding multi-part handle attached to the proximal ends of the tube and actuation cable. In this closed position, the tube can be passed through the working channel of an endoscope to the proximity of the object to be removed. The cage is extended to the open position by manipulating the actuation cable in the opposite direction. The device is then manipulated until the object becomes enclosed within the cage. The endoscope and the retrieval basket containing the object are then simultaneously removed from the body.

A number of designs for the medical retrieval baskets are in use. U.S. Pat. No. 2,943,626 (1960) to Dormia discloses a retrieval basket which has a cage made of flexible elements which may extend in radial planes which pass through the axis of the tube, or may take the shape of a helix. The flexible elements are constructed of wires or narrow bands.

U.S. Pat. No. 4,590,938 (1986) to Segura et al. discloses a retrieval basket with a cage defined by a multiplicity of spaced apart flat spring strips which are outwardly bowed and extend generally axially of the tube. The cage has a generally bulbous form at its distal end.

These and other similar prior art designs have a configuration in which the flexible elements which comprise the cage are equiangularly spaced about the cage. These designs all have certain disadvantages. When the cage comprises a small number of flexible elements (typically 3 or 4), the object to be captured passes fairly easily into the cage. However, because of the small number of flexible elements and thus large spaces between them, the object can be difficult to maintain within the cage, particularly when the object is small. Conversely, when the cage comprises a larger number of flexible elements (typically 5 or more), the object can be maintained within the cage more easily. However, because of the large number of flexible elements and thus smaller spaces between them, the object can be difficult to capture within the cage.

Certain prior art retrieval baskets have attempted to provide a cage configuration which facilitated both capturing and maintaining the object within the basket. U.S. Pat. No. 4,347,846 (1982) to Dormia discloses a cage configuration similar to that of U.S. Pat. No. 2,943,626, except that the flexible elements are disposed in pairs, one element of each pair spiraled in a clockwise direction and the other element spiraled in a counter-clockwise direction. The flexible elements of each pair are arranged so that they intersect each other in the distal half of the cage. The intent of this design is that the object can be captured in the proximal portion of the cage, and the intersecting elements in the distal portion of the cage will facilitate maintaining the object within the cage when it is partially closed. However, this configuration has certain disadvantages, which may explain why it is not currently marketed in the U.S. When the cage is in the completely retracted position within the tube, its cross-sectional area is much larger than that of a cage with the same number of similarly sized, non-intersecting elements. Very small tube diameters (typically 1 millimeter or less) are clearly desirable to allow passage through the working channels of small diameter endoscopes. In order to have a tube of the desired size with a cage having intersecting elements, the elements themselves would have to be significantly smaller than with other prior art designs. This would result in the elements exerting less dilating force on the tissue surrounding the object when the cage is expanded. In some applications, the elements might not exert enough force to open the cage completely, thus hindering the capture of the object. This design has the further disadvantage of being difficult to manufacture.

U.S. Pat. No. 5,496,330 (1996) to Bates et al. discloses a configuration in which a plurality of generally widely spaced strands form a helical shaped cage. Each of the strands consists of a plurality of elements which are closely angularly spaced throughout the length of the cage. Typical embodiments of this design are three or four strands, each of which consist of two elements. This does increase the number of contact points the basket has with the object without decreasing the size of the of the spacing between strands. However, there are certain disadvantages with this design. When three strands are used, the spacing between the strands is still rather large, allowing objects to slip through between the strands. And when four strands are used, a total of eight flexible elements are needed, more than are typically used in the other prior art baskets. In order to fit inside the same size tube, the diameter of the individual flexible elements must be reduced, which reduces their strength.

Additionally, all of the prior art baskets have a further disadvantage. Frequently, the objects to be retrieved are of irregular shape, such as urinary or biliary calculi. It is not uncommon that a particular object is difficult to secure with one type of basket, while another type of basket readily secures the same object. For example, a particular portion of an irregularly shaped object may be readily secured with two closely spaced elements of a basket. Other geometries exist in which a single element is more effective. The prior art retrieval baskets all have the limitation that each of the flexible elements presents the same configuration to the object. If a particular difficult to grasp area of the object is not effectively secured by one part of the cage, rotating the cage to use another part will have little effect, since each area of the cage presents a similar configuration.

OBJECTS AND ADVANTAGES

Accordingly, several objects and advantages of the present invention are:
(a) to provide a novel medical retrieval basket which facilitates both the capture of an object and maintaining the object within the basket;
(b) to provide a novel medical retrieval basket which is capable, by means of rotation, of presenting differing configurations of flexible elements to a given portion of the object to be retrieved;

(c) to provide a novel medical retrieval basket which optimizes the combination of the number of flexible elements and the size, spacing and cross sectional shape of the elements; and (d) to provide a novel medical retrieval basket which can effectively dilate tissue surrounding the object to be captured in order to facilitate capture of the object.

Further objects and advantages are to provide a medical retrieval basket of the type described herein which is of simple design, is simple and inexpensive to manufacture, and is easy to use. Still further objects and advantages will become apparent from a consideration of the ensuing description and drawings.

BRIEF DESCRIPTION OF THE DRAWINGS

FIGS. 5A–5D are other examples shown in a similar manner as FIGS. 3 and 4 of various possible cross sections of the wires used to form the cage according to the invention.

Figure 1:
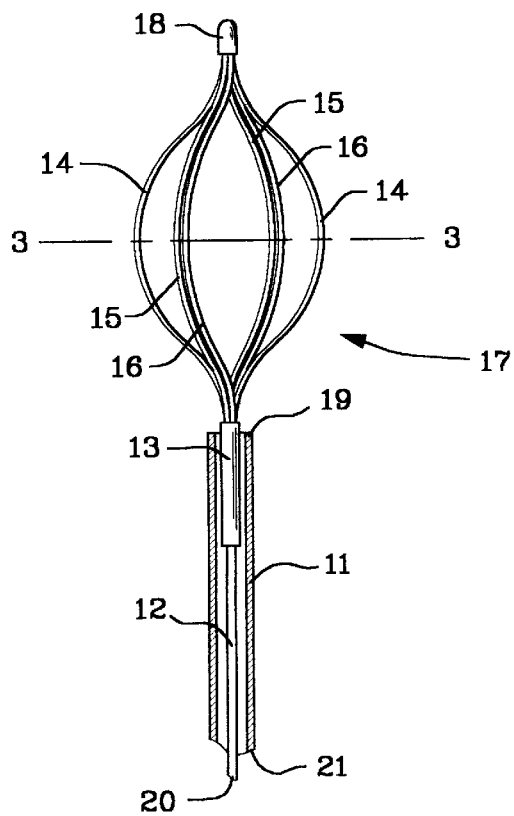
FIG. 1 shows a view in perspective of the distal end of a medical retrieval device according to the invention.

REFERENCE NUMERALS IN DRAWINGS 11 tube
12 cable
13 cylinder
14 wire or flexible element (widely spaced single member)
15 wire or flexible element (closely spaced member of a plural set)
16 wire or flexible element (closely spaced member of a plural set)
17 cage or basket
18 tip
19 distal end of tube
20 proximal end of cable
21 proximal end of tube Description FIGS. 1 to 5

FIG. 1 shows the distal end of a typical embodiment of the invention. An actuation wire or cable 12 passes through a sheath or tube 11. Cable 12 consists of one or more wires constructed of stainless steel, nickel titanium alloy, or another metal, and has a proximal end 20. Tube 11 is constructed of polymeric tubing, a stainless steel coil, or other flexible material which has a lumen through its entire length, and has a distal end 19 and a proximal end 21. Cable 12 is joined to wires or flexible elements 14, 15, 16 with a cylinder 13 by means of soldering, welding, swaging or other means. Flexible elements 14, 15, 16 extend from cylinder 13 to form an expanded basket or cage 17. At the distal end of cage 17 there is an optional tip 18 which is secured to flexible elements 14, 15, 16 by means of soldering, welding, swaging or other means. Tip 18 is blunted at the end to prevent tissue trauma. A filiform tip (not shown) could also be used for this purpose. Flexible elements 14, 15, 16 are constructed of stainless steel, nickel titanium or other shape memory alloys, which in this embodiment have a circular cross section. Proximal end of tube 21 and proximal end of cable 20 can be extended for attachment to an optional actuating mechanism (not shown), such as a sliding handle, to facilitate the movement of cable 12 inside tube 11.

Cage 17 is shown in its fully expanded position with all of flexible elements 14, 15, 16 outwardly disposed from distal end of the tube 19. In this embodiment, flexible elements 14, 15, 16 are longitudinally aligned between the proximal and distal ends of cage 17. Flexible elements 14 are relatively widely spaced from adjacent flexible elements 15 and 16. This wider spacing should be sufficient for the passage of an object, for example ureteral calculus, into cage 17. Flexible elements 15 and 16 are more closely spaced to each other so it is expected that the object to be removed would not pass between them. The spacing of flexible elements 14, 15, 16 can be readily seen in FIG. 3, which is a cross sectional view taken on line 3—3 in FIG. 1. Flexible elements 14, 15, 16 are given the desired configuration using means familiar to those skilled in the art.

Figure 2:
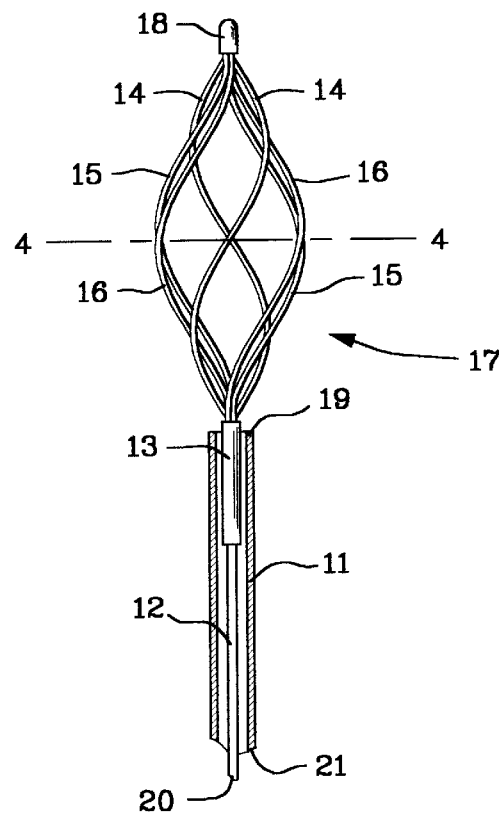
FIG. 2 shows the invention in a helical configuration.
Figure 4:
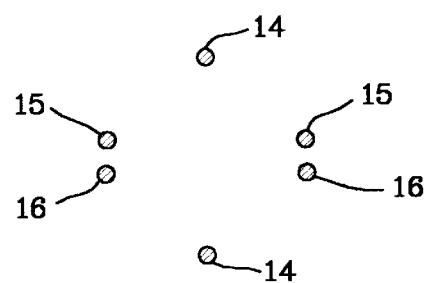
FIG. 4 is a cross sectional view taken on line 4—4 in FIG. 2.

FIG. 2 shows the distal end of another typical embodiment of the invention. This embodiment is similar to that shown in FIG. 1, except flexible elements 14, 15, 16 are arranged in a helical configuration. Again, flexible elements 14 are relatively widely spaced from adjacent flexible elements 15 and 16, and flexible elements 15 and 16 are more closely spaced to each other. FIG. 4 is a cross sectional view taken on line 4—4 in FIG. 2, and readily shows the spacing of flexible elements 14, 15, 16.

Figure 3:
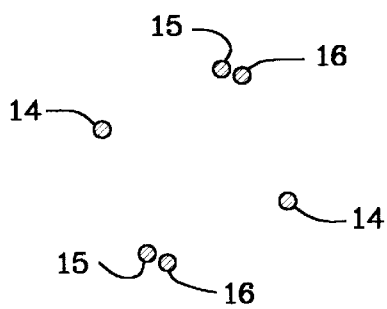
FIG. 3 is a cross sectional view taken on line 3—3 in FIG. 1.

FIGS. 5A to 5D show other examples in a similar manner as FIGS. 3 and 4 of various possible cross sections of the flexible elements used to form the cage according to the invention. As can be seen, the number of flexible elements, their size, cross sectional shape and orientation can be varied. In addition, flexible elements of differing size and/or cross sectional shape can be used within the same cage to provide a number of different configurations. Many other combinations not shown here are also within the scope of the invention.

Operation FIGS. 1 and 2

To operate the device, proximal end of cable 20 is pulled relative to proximal end of tube 21 in order to retract cage 17 into tube 11 until tip 18 is located near distal end of tube 19. This causes flexible elements 14, 15,16 to collapse within tube 11. If, for example, the object to be removed is a ureteral calculus, the device is introduced in this retracted position through the working channel of an endoscope into the ureter. The collapsed cage would be placed next to or beyond the calculus.

Proximal end of cable 20 is pushed forward relative to proximal end of tube 21 to extend cage 17 from distal end of tube 19. Flexible elements 14, 15, 16 spread outwardly to attempt to resume their previous shape and configuration by reason of their shape memory and elasticity. The lumen of the ureter or other body passage may restrict cage 17 from fully expanding. However, the unique configuration of cage 17 according to the invention allows flexible elements 14, 15, 16 to exert considerable dilation force on the body passage, as will be further discussed below.

Cage 17 is then manipulated until the object passes through the wide space between flexible elements 14 and 15 or 14 and 16. This manipulation is accomplished by manipulating proximal end of cable 20, and may include pushing, pulling or rotating. When cable 12 is constructed of nickel titanium, rotation of proximal end of cable 20 will give more precise control of the rotation of cage 17. This allows for ease of positioning cage 17 in order to pass the object inside cage 17. Proximal end of cable 20 may then be pulled to partially retract cage 17 into distal end of tube 19 in order to securely hold the object within cage 17 by bringing flexible elements 14, 15, 16 into contact with the object. If the object proves difficult to hold, cage 17 can be rotated in order to present a different configuration of flexible elements 14, or 15 and 16, to a particular portion of the object, which may better facilitate securing the object. Again, when cable 12 is constructed of nickel titanium, rotation of cage 17 can be more precisely controlled. Once the object is secured within cage 17, the device is then withdrawn to remove the object from the patient.

When the flexible elements are of differing size and/or cross sectional shape, for example as shown in FIGS. 5A to 5D, rotation of the cage will similarly present a different configuration of flexible elements to a particular portion of the object, which may better facilitate securing the object.

It can be seen from the above description that the invention provides a medical retrieval basket which facilitates both capturing and maintaining the object within the cage. This is accomplished using a unique cage configuration which allows the cage to present differing configurations of flexible elements to certain portions of the object by means of rotating the cage. It can further be seen that this is accomplished without using a large number of flexible elements to construct the cage. The sizes of the individual flexible elements are limited since the tube is of fairly small diameter (typically 1 millimeter or less). Thus, limiting the total number of flexible elements allows the size of each flexible element to be maximized. This gives the desirable result that each flexible element is able to exert considerable outward force to dilate the tissue surrounding the object, facilitating capture of the object.

Summary, Ramifications, and Scope

Accordingly, the reader will see that the medical retrieval basket of this invention facilitates both capturing and maintaining an object by providing a novel cage design which is capable, by means of rotation, of presenting differing configurations of flexible elements to a given portion of the object. Furthermore, this medical retrieval basket has the additional advantages in that it optimizes the combination of the number of flexible elements and the size, spacing and cross sectional shape of the elements;

it can effectively dilate tissue surrounding the object to be captured in order to facilitate capture of the object; and it functions similarly to the most commonly used prior art designs.

Although the description above contains many specificities, these should not be construed as limiting the scope of the invention, but as merely providing illustrations of some of the presently preferred embodiments of this invention. For example, different numbers of flexible elements may be used; other cross sectional shapes may be used for the flexible elements, other combinations of the number, size, spacing and cross sectional shape of the flexible elements may be used; other overall configurations for the cage may be used; additional materials and joining methods may be used; the tip may have other configurations; the tip may be eliminated; the device may be used without an endoscope; objects other than those mentioned or in different locations in the body may be retrieved, etc.

Thus the scope of the invention should be determined by the appended claims and their legal equivalents, rather than by the examples given.

What is claimed is:

1. A medical retrieval basket for extracting an object from a body comprising:

a cage having a longitudinal axis and an expandable portion consisting of a plurality of flexible elements which are outwardly disposed to form a space for entrapping said object, a tubular means for the collapsing of said flexible elements when withdrawn into said tubular means, an actuation means to enable the movement of said flexible elements into and out of said tubular means and to enable rotation of said cage, the impivement wherein the flexible elements, when outwardly disposed, include a plurality of flexible elements, forming a plural set, which are spaced relatively closely to each other and spaced relatively far from adjacent flexible elements outside of the plural set, the flexible elements, when outwardly disposed, also including a single flexible element spaced relatively far from adjacent flexible elements, wherein there are a plurality of plural sets and at least one single flexible element spaced around said longitudinal axis, whereby rotation of said actuation means will cause rotation of said cage in order to present either a single flexible element or a said plural set to the object being removed.

2. The medical retrieval basket of claim 1 wherein the actuation means is a cable containing a shape memory alloy.

3. The medical retrieval basket of claim 1 further including a substantially cylindrical tip at the distal end of said cage.

4. The medical retrieval basket of claim 1 wherein said flexible elements are in an approximately helical configuration.

5. The medical retrieval basket of claim 1 wherein said flexible elements are metallic with the materials being selected from a group consisting of stainless steel and shape memory alloys .

6. A medical retrieval basket for extracting an object from a body comprising:

a cage having a longitudinal axis and an expandable portion consisting of a plurality of flexible elements which are outwardly disposed to form a space for entrapping said object, a tubular means for the collapsing of said flexible elements when withdrawn into said tubular means, an actuation means to enable the movement of said flexible elements into and out of said tubular means and to enable rotation of said cage, the improvement wherein each of said flexible elements has a predetermined cross sectional shape and said cage incorporates a plurality of the flexible element cross sectional shape, whereby rotation of said actuation means about said longitudinal axis will cause rotation of said cage in order to present differing said flexible element cross sectional shape to the object being removed.

7. The medical retrieval basket of claim 6 wherein the actuation means is a cable containing a shape memory alloy.

8. The medical retrieval basket of claim 6 further including a substantially cylindrical tip at the distal end of said cage.

9. The medical retrieval basket of claim 6 wherein said flexible elements are in an approximately helical configuration.

10. The medical retrieval basket of claim 6 wherein said flexible elements are metallic with the materials being selected from a group consisting of stainless steels and other shape memory alloys.

\* \* \* \* \*